US 7,118,705 B2

(12) United States Patent
Lin et al.

(10) Patent No.: US 7,118,705 B2
(45) Date of Patent: Oct. 10, 2006

(54) METHOD FOR MAKING A MOLDED CALCIUM PHOSPHATE ARTICLE

(75) Inventors: Jiin-Huey Chern Lin, Winnetka, IL (US); Chien-Ping Ju, Carbondale, IL (US); Chih-Hung Tsai, Taichung (TW)

(73) Assignee: Calcitec, Inc., Austin, TX (US)

( * ) Notice: Subject to any disclaimer, the term of this patent is extended or adjusted under 35 U.S.C. 154(b) by 158 days.

(21) Appl. No.: 10/633,511

(22) Filed: Aug. 5, 2003

(65) Prior Publication Data

US 2005/0029701 A1 Feb. 10, 2005

(51) Int. Cl.
*A61F 2/28* (2006.01)
*B29C 39/02* (2006.01)

(52) U.S. Cl. .................................. 264/333; 623/16.11
(58) Field of Classification Search .............. 623/16.11, 623/17.11, 23.47, 23.51, 23.62; 264/333
See application file for complete search history.

(56) References Cited

U.S. PATENT DOCUMENTS

| 3,679,360 A | 7/1972 | Rubin et al. |
| 4,371,484 A | 2/1983 | Inukai et al. |
| 4,481,175 A | 11/1984 | Iino et al. |
| 4,518,430 A | 5/1985 | Brown et al. |
| 4,553,272 A | 11/1985 | Mears |
| 4,612,053 A | 9/1986 | Brown et al. |
| 4,623,553 A | 11/1986 | Ries et al. |
| RE33,161 E | 2/1990 | Brown et al. |
| RE33,221 E | 5/1990 | Brown et al. |
| 4,959,104 A | 9/1990 | Iino et al. |
| 5,017,518 A | 5/1991 | Hirayama et al. |
| 5,053,212 A | 10/1991 | Constantz et al. |
| 5,092,888 A | 3/1992 | Iwamoto et al. |
| 5,149,368 A | 9/1992 | Liu et al. |
| 5,152,791 A | 10/1992 | Hakamatsuka et al. |
| 5,164,187 A | 11/1992 | Constantz et al. |
| 5,180,426 A | 1/1993 | Sumita |
| 5,262,166 A | 11/1993 | Liu et al. |
| 5,336,264 A | 8/1994 | Constanz et al. |
| 5,338,356 A | 8/1994 | Hirano et al. |
| 5,342,441 A | 8/1994 | Mandai et al. |
| 5,409,982 A | 4/1995 | Imura et al. |
| 5,476,647 A | 12/1995 | Chow et al. |
| 5,492,768 A | 2/1996 | Okimatsu et al. |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,605,713 A | 2/1997 | Boltong |
| 5,607,685 A | 3/1997 | Cimbollek et al. |
| 5,652,016 A | 7/1997 | Shiro et al. |
| 5,683,461 A | 11/1997 | Lee et al. |
| 5,683,496 A | 11/1997 | Ison et al. |
| 5,695,729 A | 12/1997 | Chow et al. |
| 5,697,981 A | 12/1997 | Ison et al. |
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A * | 10/1998 | Constantz et al. .......... 423/308 |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,018,095 A | 1/2000 | Lerch et al. |
| 6,027,742 A | 2/2000 | Lee et al. |
| 6,077,989 A | 6/2000 | Kandel et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,149,688 A | 11/2000 | Brosnahan et al. |
| 6,162,258 A | 12/2000 | Scarborough et al. |

(Continued)

FOREIGN PATENT DOCUMENTS

| EP | 0267624 | 5/1988 |
| JP | 06-228011 | 8/1994 |
| WO | WO 03/055418 | 7/2003 |

OTHER PUBLICATIONS

Sugawara et al., "Formation of Hydroxyapatite in Hydrogels from Tetracalcium Phosphate/Dicalcium Phosphate Mixtures," J. Nihon Univ. Sch. Dent., vol. 31, 372–381, 1989.

Chow et al. "A Natural Bone Cement–A Laboratory Novelty Led to the Development of Revolutionary New Biomaterials", J. Res. Natl. Inst. Stand. Technol., 2001, vol. 106, pp. 1029–1033.

(Continued)

*Primary Examiner*—Mary Lynn Theisen
(74) *Attorney, Agent, or Firm*—Meyertons, Hood, Kivlin, Kowert & Goetzel, P.C.; Eric B. Meyertons

(57) ABSTRACT

The present invention discloses a method for making a molded calcium phosphate article including impregnating a rigid shaped article of calcium phosphate in an impregnating liquid for a period of time so that a compressive strength of the resulting impregnated article removed from the impregnating liquid is increased compared to that of the rigid shaped article. The molded calcium phosphate article made according to the present invention may be used as a medical implant or a reinforcing constituent of a composite.

32 Claims, No Drawings

U.S. PATENT DOCUMENTS

| | | | |
|---|---|---|---|
| 6,277,149 B1 | 8/2001 | Boyle et al. | |
| 6,294,041 B1 | 9/2001 | Boyce et al. | |
| 6,294,187 B1 | 9/2001 | Boyce et al. | |
| 6,323,146 B1 | 11/2001 | Pugh et al. | |
| 6,325,987 B1 | 12/2001 | Sapieszko et al. | |
| 6,325,992 B1 | 12/2001 | Chow et al. | |
| 6,332,779 B1 | 12/2001 | Boyce et al. | |
| 6,340,648 B1 * | 1/2002 | Imura et al. | 501/80 |
| 6,379,453 B1 | 4/2002 | Lin et al. | |
| 6,440,444 B1 | 8/2002 | Boyce et al. | |
| 6,458,162 B1 | 10/2002 | Koblish et al. | |
| 6,478,825 B1 | 11/2002 | Winterbottom et al. | |
| 6,495,156 B1 | 12/2002 | Wenz et al. | |
| 6,530,955 B1 | 3/2003 | Boyle et al. | |
| 6,547,866 B1 * | 4/2003 | Edwards et al. | 106/35 |
| 6,569,489 B1 | 5/2003 | Li | |
| 6,585,992 B1 | 7/2003 | Pugh et al. | |
| 6,616,742 B1 * | 9/2003 | Lin et al. | 106/35 |
| 6,648,960 B1 * | 11/2003 | Lin et al. | 106/690 |
| 6,670,293 B1 | 12/2003 | Edwards et al. | |
| 6,840,995 B1 | 1/2005 | Lin et al. | |
| 2002/0019635 A1 | 2/2002 | Wenstrom, Jr. et al. | |
| 2002/0073894 A1 | 6/2002 | Genge et al. | |
| 2002/0137812 A1 | 9/2002 | Chow et al. | |
| 2002/0169066 A1 | 11/2002 | Cassidy et al. | |
| 2003/0019396 A1 | 1/2003 | Edwards et al. | |
| 2003/0021824 A1 | 1/2003 | Lacout et al. | |
| 2003/0031698 A1 | 2/2003 | Roeder et al. | |
| 2003/0039676 A1 | 2/2003 | Boyce et al. | |
| 2003/0055512 A1 | 3/2003 | Genin et al. | |
| 2003/0074081 A1 | 4/2003 | Ayers et al. | |
| 2003/0078317 A1 * | 4/2003 | Lin et al. | 523/116 |
| 2003/0120351 A1 | 6/2003 | Tofighi | |
| 2003/0121450 A1 | 7/2003 | Lin et al. | |
| 2004/0003757 A1 | 1/2004 | Lin et al. | |
| 2004/0031420 A1 | 2/2004 | Lin et al. | |
| 2004/0175320 A1 | 9/2004 | Lin et al. | |
| 2004/0180091 A1 | 9/2004 | Lin | |
| 2004/0186481 A1 | 9/2004 | Lin et al. | |

OTHER PUBLICATIONS

Gburek et al., "Mechanical Activation of Tetracalcium Phosphate," J. Am. Ceramics Soc., vol. 87(2), pp. 311–313.

Sugawara et al., "Calcium Phosphate Cement: An In Vitro study of Dentin Hypersensitivity", The Journal of the Japanese Society for Dental Materials and Devices, 1989, vol. 8, pp. 282–294.

Pickel et al., "The Effect of a Chewing Gum Containing Dicalcium Phosphate on Salivery Calcium and Phosphate", Ala. J. Med. Sci. 1965, vol. 2, pp. 286–287.

Matsuya et al., "Effects of pH on the Reactions of Tetracalcium Phosphate and Dicalcium Phosphate", IADR Abstract 1991.

Sugawara et al., "Formation of Hydroxyapatite in Hydrogels from Tetracalcium Phosphate/Dicalcium Phosphate Mixtures," J. Nihon. Univ. Sch. Dent., 1989, vol. 31, pp. 372–381.

Hong et al., The Periapical Tissue Reactions to a Calcium Phosphate Cement in the Teeth of Monkeys, J. Biomed Mater Res. Apr. 1991, vol. 25(4), pp. 485–498.

DeRijk, et al., "Clinical Evalution of a Hydroxyapatite for Precipitate for the Treatment of Dentinal Hypersensitivity, Biomedical Engineering v. Recent Developments," Proc of 5th Southern Biomedical Engineering Conference, 1986, pp. 336–339. (Pergamon Press, New York).

Groninger et al. "Evaluation of the Biocompatibity of a New Calcium Phosphate Setting Cement," J. Dent Res. 1984, 63 Abst. No. 270 (4 pages).

Costantino et al., Evaluation of a New Hydroxyapatite Cement: Part III, Cranioplasty ina Cat Model, The Fifth Intl. Symposium on Facial Plastic Reconstructive Surgery of the Head and Neck, Toronto, Canada 1989, (18 pages).

Shindo, et al., "Facial Skeletal Augmentation Using Hydroxyapatite Cement," Arch. Otalaryngol. Head Neck Srug. 1993, vol. 119, pp. 185–190.

Briner et al., "Significance of Enamel Remineralization", J. Dent. Res. 1974, vol. 53, pp. 239–243.

Silverstone, "Remineralization Phenomena", Caries Res. 1977, vol. 11 (Supp. 1), pp. 59–84.

Costantino et al., "Hydroxyapatite Cement—Basic Chemistry and Histologic Properties," Arch. of Otolarngology—Head & Neck Sugery, 1991, vol. 117, pp. 379–394.

Friedman et al., "Hydroxyapatite Cement II. Obliteration and Reconstruction of the Cat Frontal Sinus," Arch. of Otolaryngology—Heady & Neck Surgery, 1991, vol. 117, pp. 385–389.

Contantino et al., "Experimental Hydroxyapatite Cement Cranioplasty," Plastic and Reconstructive Surgery, 1992, vol. 90, No. 2, pp. 174–185.

Miyazaki et al., "An Infrared Spectroscopic Study of Cement Formation of Polymeric Calcium Phosphate Cement," Jour of the Jap. Scoiety for Dent Mats & Devices, 1992, vol. II, No. 2. (8 pages).

Driskell et al., "Development of Ceramic and Ceramic Composite Devices for Maxillofacial Applications", J. Biomed. Mat. Res. 1972, vol. 6, pp. 345–361.

Hiatt et al., "Root Preparation I. Obduration of Dentinal Tubules in Treatment of Root Hypersensitivity", J. Periodontal, 1972, vol. 43, pp. 373–380.

Patel et al., "Solubility of $CaHPO_4$ $2H_2O$ in the Quaternary System $Ca(OH)_2$ —$H_3PO_4$ —NaCl—$H_2O$ at 25 °C.," Nat. Bur. Stands. 1974, vol. 78A, pp. 675–681.

Salyer et al., "Porous Hydroxyapatite as an Onlay Bone–Graft Substitue for Maxillofacial Surgery," Presented at the 54th Annual Scientific Meeting of the American Society of Plastic and Reconstructive Surgeons, Kansas City, Missouri, 1985, pp. 236–244.

Kenney et al., "The Use of a Porous Hydroxyapatite Implant in Periodontal Defects," J. Periodontal, 1988, pp. 67–72.

Zide et al., "Hydroxyapatite Cranioplasty Directly Over Dura," J. Oral Maxillofac Surg. 1987, vol. 45, pp. 481–486.

Waite, et al., "Zygomatic Augmentation with Hydroxyapatite," J. Oral Maxillofac Surg 1986, pp. 349–352.

Verwoerd, et al. "Porous Hydroxyapatite–perichondrium Graft in Cricoid Reconstruction, Acta Otolaryngol" 1987, vol. 103, pp. 496–502.

Grote, "Tympanoplasty With Calcium Phosphate," Arch Otolaryngology 1984, vol. 110, pp. 197–199.

Kent et al., "Alveolar Ridge Augmentation Using Nonresorbable Hydroxyapatite with or without Autogenous Cancellous Bone," J. Oral Maxillofac Surg 1983, vol. 41, pp. 629–642.

Piecuch, "Augmentation of the Atrophic Edentulous Ridge with Porus Replamineform Hydroxyapatite (Interpore–200)", Dental Clinics of North America 1985, vol. 30(2), pp. 291–305.

Misch, "Maxillary Sinus Augementation for Endosteal Implants: Organized Alternative Treatment Plans," Int J Oral Implant 1987, vol. 4(2), pp. 49–58.

Chohayeb, A. A. et al., "Evaluation of Calcium Phosphate as Root Canal Sealer–Filler Material," J Endod 1987, vol. 13, pp. 384–386.
Brown et al., "Crystallography of Tetracalcium Phosphate," Journal of Research of the National Bureau of Standards. A Physics and Chemistry. 1965, vol. 69A, pp. 547–551.
Sanin et al. "Particle Size Effects on pH and Strength of Calcium Phosphate Cement," IADR Abstract 1991.
Chow et al., "X–ray Diffraction and Electron Microscopic Characterization of Calcium Phosphate Cement Setting Reactions," IADR Abstract, 1987. (1 page).
Block et al. "Correction of Vertical Orbital Dystopia with a Hydroxyapatite Orbital Floor Graft," J. Oral Maxillofac Surg 1988, vol. 46, pp. 420–425.
Brown, "Solubilities of Phosphates and Other Sparingly Soluble Componds", Environmental Phosphorous Handbook 1973, pp. 203–239. (John Wiley & Sons, New York).
Gregory et al., "Solubility of $CaHPO_4$ $2H_2O$ in the System $Ca(OH)_2$ —$H_3PO^4$ —$H_2O$ at 5, 15, 25, and 37.5 °C., " J. Res. Nat. Bur. Stand. 1970, vol. 74A, pp. 461–475.
Gregory et al., "Solubility of $\beta$—$Ca_3(PO_4)_2$ in the System $Ca(OH)_2$ —$H_3PO_4$ —$H_2O$ at 5, 15, 25 and 37°C.," J. Res. Nat. Bur. Stand., 1974, vol. 78A, pp. 667–674.
McDowell et al., "Solubility of B—$Ca_5(PO_4)_3$ OH in the System $Ca(OH)_2$ —$H_3PO_4$ —$H_2O$ at 5, 15, 25 and 37 °C.," J. Res. Nat. Bur. Stand. 1977, vol. 91A, pp. 273–281.
McDowell et al., "Solubility Study of Calcium Hydrogen Phosphate. Ion Pair Formation," Inorg. Chem. 1971, vol. 10, pp. 1638–1643.
Moreno et al., "Stability of Dicalcium Phosphate Dihydrate in Aqueous Solutions and Solubility of Octocalcium Phosphate," Soil Sci. Soc. Am. Proc. 1960, vol. 21, pp. 99–102.
Chow et al, "Self–Setting Calcium Phosphate Cements," Mat. Res. Soc. Symp. Proc. pp. 3–23.
Miyazaki et al., "Chemical Change of Hardened PCA/CPC Cements in Various Storing Solutions", The Journal of the Japanese Soc. for Dental Materials and Devices, 1992, vol. 11, No. 2.
Fukase et al, "Thermal Conductivity of Calcium Phosphate Cement", IADR Abstract, 1990 (1 page).
Sugawara et al. "Biocompatibility and Osteoconductivity of Calcium Phosphate Cement", IADR Abstract 1990. (1 page).
Miyazaki et al., "Polymeric Calcium Phosphate Cements", IADR Abstract 1990. (1 page).
Link et al., "Composite of Calcium Phosphate Cement and Genetically Engineered Protein Bioadhesive," IADR Abstract 1991. (1 page).
Matsuya et al., "Effects of pH on the Reactions of Tetracalcium Phosphate and Dicalcium Phosphate", IADR Abstract 1991. (1 page).
Briner et al., "Significance of Enamel Remineralization", J. Dent. Res. 1974, vol. 53, pp. 239–243.
Chow, "Development of Self–Setting Calcium Phosphate Cements", Journal of The Ceramic Society of Japan, 1991, vol. 99 [10 ], pp. 954–964.
Brown et al., A New Calcium Phosphate, Water Setting Cement, Cements Research Progress 1986, P. W. Brown, Ed., Westerville, Ohio: American Ceramic Society, 1988, pp. 352–379.
Sugawara et al., "Evaluation of Calcium Phosphate as a Root Canal Sealer–Filler Material" IADR/AADR Abstract, 1987, (3 pages).
Sugawara et al., "In Vitro Evaluation of the Sealing Ability of a Calcium Phosphate Cement When Used as a Root Canal Sealer Filler," J. Endodontics, 1989, vol. 16, pp. 162–165.
Chow, "Calcium Phosphate Materials: Reactor Response" Adv Dent Res 1988, vol. 2(1), pp. 181–184.
Fukase et al., "Setting Reactions and Compressive Strengths of Calcium Phosphate Cements", J Dent Res 1990, vol. 69(12), pp. 1852–1856.
Miyazaki et al., "Chemical Change of Hardened PCA/CPC Cements in Various Storing Solutions", The Journal of the Japanese Soc. for Dental Materials and Devices, 1992, vol. 11, No. 2, pp. 48–64.
U.S. Patent and Trademark Office, "Office Communication" mailed Feb. 22, 2005,
Claims from Co–Pending U.S. Appl. No. 10/773,701, 3 pages.
Claims from Co–Pending U.S. Appl. No. 10/944,278, 3 pages.
Claims from Co–Pending U.S. Appl. No. 10/940,922, 4 pages.
Claims from Co–Pending U.S. Appl. No. 10/780,728, 6 pages.
Claims from Co–Pending U.S. Appl. No. 10/852,167, 7 pages.
Claims from Co–Pending U.S. Appl. No. 10/982,660, 3 pages.
Claims from Co–Pending U.S. Appl. No. 10/145,901, 3 pages.
Claims from Co–Pending U.S. Appl. No. 10/607,023, 1 page.
Claims from Co–Pending U.S. Appl. No. 10/414,582.
U.S. Patent and Trademark Office, "Office Communication" U.S. Appl. No. 09/615,384, mailed Jan. 16, 2003
U.S. Patent and Trademark Office, "Office Communication" U.S. Appl. No. 09/615,384, mailed Mar. 22, 2002.
U.S. Patent and Trademark Office, "Office Communication" U.S. Appl. No. 09/615,384, mailed Oct. 18, 2001.
U.S. Patent and Trademark Office, "Office Communication" U.S. Appl. No. 10/328,019, mailed Feb. 25, 2004.
U.S. Patent and Trademark Office, "Office Communication" U.S. Appl. No. 10/414,582, mailed Jun. 17, 2004.
U.S. Patent and Trademark Office, "Office Communication" U.S. Appl. No. 10/607,023, mailed Jul. 18, 2004.
PCT/US04/11637 International Search Report/Written Opinion, mailed Oct. 8, 2004.

* cited by examiner

METHOD FOR MAKING A MOLDED CALCIUM PHOSPHATE ARTICLE

FIELD OF THE INVENTION

The present invention is related to a calcium phosphate article for use as medical implant, and in particular to a method of making a molded calcium phosphate block having a superior compressive strength for use as medical implant.

BACKGROUND OF THE INVENTION

It is advantageous if a bone implant is bioresorbable and is supportive at the same time. Accordingly, an article made of calcium phosphate will be preferable than that made of a metal, if the former has strength which is comparable to a human cortical bone. One way of making such a bone implant made of calcium phosphate is by sintering a calcium phosphate, particularly a hydroxyapatite (HA), powder into a block material at a temperature generally greater than 1000° C. Despite the fact that the high temperature-sintered HA block material has an enhanced strength, the bioresorbability of the material is largely sacrificed, if not totally destroyed, due to the elimination of the micro- and nano-sized porosity during the sintering process.

SUMMARY OF THE INVENTION

A primary objective of the invention is to provide a calcium phosphate article or block for use as a bone implant, which is free from the aforesaid drawbacks in the prior art.

This objective is accomplished by providing a novel method for making a calcium phosphate article, which involves impregnating an article molded from a paste of calcium phosphate cement (CPC) in a liquid for a period of time, so that the compressive strength of the CPC block is significantly improved after removing from the liquid.

Features and advantages of the present invention are as follows:

1. The calcium phosphate block made according to the present invention can transform into an apatite-dominated material shortly after immersion in physiological solution or after implantation.
2. The calcium phosphate block made according to the present invention exhibits a high strength comparable to that of human cortical bone (about 110–170 MPa). The strength is adjustable by adjusting process parameters.
3. The calcium phosphate block made according to the present invention possesses a significant amount of micro- and nano-sized porosity, that improves bioresorbability thereof. Conventional high temperature-sintered HA block, on the other hand, does not possess sufficient micro/nano-sized porosity and is not bioresorbable.
4. The resorption rate is adjustable by adjusting process parameters.
5. Any complicated-shaped article can be easily fabricated with no need of machining. Once a mold of desired size and shape is prepared, mass production is easy.
6. A wide range of medical application includes bone dowel, spacer, cavity filler, artificial disc and fixation devices for spine and other locations, to name a few.

DETAILED DESCRIPTION OF THE INVENTION

The present invention discloses a method for making a molded calcium phosphate article comprising impregnating a rigid shaped article of calcium phosphate with an impregnating liquid for a period of time so that a compressive strength of the resulting impregnated article removed from the impregnating liquid is increased compared to that of the rigid shaped article without said impregnating treatment.

Preferably, the impregnating liquid is an acidic solution, a basic solution, a physiological solution, an organic solvent, or a substantially pure water. Preferably, the impregnating liquid comprises at least one of Ca and P sources. Preferably, the impregnating liquid is a Hanks' solution, a HCl aqueous solution or an aqueous solution of $(NH_4)_2HPO_4$.

Preferably, the rigid shaped article of calcium phosphate is a molded article from a paste of calcium phosphate cement.

Preferably, the impregnating is carried out for a period longer than 10 minutes, and more preferably for about 12 hours to 96 hours.

Preferably, the impregnating is carried out at room temperature.

According to one aspect of the present invention, a method for making a molded calcium phosphate article comprising the following steps:

(a) preparing a powder comprising at least one Ca source and at least one P source, or at least one calcium phosphate source;
(b) mixing said powder with a setting liquid to form a paste, wherein said paste undergoes a hardening reaction;
(c) molding said paste into an article in a mold of a desired shape and size before said hardening reaction is complete;
(d) impregnating the resulting hardened article from step (c) with an impregnating liquid to allow strength of said article to increase; and (e) removing said article from said impregnating liquid.

Preferably, said calcium phosphate source in step (a) comprises one or more calcium phosphates selected from the group consisting of alpha-tricalcium phosphate (α-TCP), beta-tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.

Preferably, the calcium phosphate source comprises at least one calcium phosphate particle having calcium phosphate whiskers on the surface of said calcium phosphate particle, wherein said calcium phosphate whiskers have a length of about 1–5000 nm and a width of about 1–500 nm.

Preferably, the setting liquid in step (b) is an acidic solution, a basic solution, or a substantially pure water.

An acidic solution suitable for use in the present invention is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate ($NaH_2PO_4 \cdot H_2O$), sodium dihydrogen phosphate dihydrate, sodium dihydrogen phosphate dehydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid and their mixture.

A basic solution suitable for use in the present invention is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4 \cdot 12H_2O$), dipotassium hydrogen phosphate ($K_2HPO_4$), potassium hydrogen phosphate trihydrate ($K_2HPO_4 \cdot 3H_2O$), potassium phosphate tribasic ($K_3PO_4$), diammonium hydrogen phosphate (($NH_4)_2HPO_4$), ammonium phosphate trihydrate (($NH_4)_3PO_4 \cdot 3H_2O$), sodium bicarbonate ($NaHCO_3$), sodium hydrogen carbonate ($NaHCO_3$), sodium carbonate $Na_2CO_3$, and their mixture.

Step (c) of the method of the present invention preferably further comprises removing said article from said mold.

Step (c) of the method of the present invention preferably further comprises removing a portion of liquid from said paste, so that a liquid/powder ratio of said paste decreases.

Step (c) of the method of the present invention preferably further comprises pressurizing said paste in said mold, preferably between 1 and 500 MPa, before said hardening reaction is complete to remove a portion of liquid from said paste, so that a liquid/powder ratio of said paste decreases. More preferably, step (c) further comprises heating said paste during said pressurizing.

Step (c) of the method of the present invention preferably further comprises heating said paste during molding.

Step (d) of the method of the present invention preferably further comprises heating the impregnating liquid, preferably at a temperature between 30 and 90° C. during said impregnating.

The method of the present invention may further comprise drying said article after removing said article from said impregnating liquid.

The method of the present invention may further comprise heating said article, preferably at a temperature between 50 and 500° C., after removing said article from said impregnating liquid.

The molded calcium phosphate article made according to the method of the present invention may be used as a medical implant or a reinforcing constituent of a composite.

The following examples are intended to demonstrate the invention more fully without acting as a limitation upon its scope, since numerous modifications and variations will be apparent to those skilled in this art.

PREPARATIVE EXAMPLE 1

Preparation of TTCP Powder

A $Ca_4(PO_4)_2O$ (TTCP) powder was prepared by mixing $Ca_2P_2O_7$ powder with $CaCO_3$ powder uniformly in ethanol for 24 hours followed by heating to dry. The mixing ratio of $Ca_2P_2O_7$ powder to $CaCO_3$ powder was 1:1.27 (weight ratio) and the powder mixture was heated to 1400° C. to allow two powders to react to form TTCP.

PREPARATIVE EXAMPLE 2

Preparation of Conventional TTCP/DCPA-Based CPC Powder (Abbreviated as C—CPC)

The resulting TTCP powder from PREPARATIVE EXAMPLE 1 was sieved and blended with dried $CaHPO_4$ (DCPA) powder in a ball mill for 12 hours. The blending ratio of the TTCP powder to the DCPA powder was 1:1 (molar ratio) to obtain the conventional CPC powder. Particles of this C-CPC powder have no whisker on the surfaces thereof.

PREPARATIVE EXAMPLE 3

Preparation of Non-Dispersive TTCP/DCPA-Based CPC Powder (Abbreviated as ND-CPC)

The TTCP powder prepared according to the method of PREPARATIVE EXAMPLE 1 was sieved and blended with dried $CaHPO_4$ (DCPA) powder in a ball mill for 12 hours. The blending ratio of the TTCP powder to the DCPA powder was 1:1 (molar ratio). The resultant powder mixture was added to a 25 mM diluted solution of phosphate to obtain a powder/solution mixture having a concentration of 3 g powder mixture per 1 ml solution while stirring. The resulting powder/solution mixture was formed into pellets, and the pellets were heated in an oven at 50° C. for 10 minutes. The pellets were then uniformly ground in a mechanical mill for 20 minutes to obtain the non-dispersive TTCP/DCPA-based CPC powder (ND-CPC). The particles of this ND-CPC powder have whisker on the surfaces thereof.

EXAMPLE 1

Effect of Immersion Time on Compressive Strength of CPA Block

To a setting solution of 1M phosphoric acid solution (pH=5.89) the ND-CPC powder from PREPARATIVE EXAMPLE 3 was added in a liquid/powder ratio (L/P ratio) of 0.4, i.e. 4 ml liquid/10 g powder, while stirring. The resulting paste was filled into a cylindrical steel mold having a length of 12 mm and a diameter of 6 mm, and was compressed with a gradually increased pressure until a maximum pressure was reached. The maximum pressure was maintained for one minute, and then the compressed CPC block was removed from the mold. At the 15$^{th}$ minute following the mixing of the liquid and powder, the compressed CPC block was immersed in a Hanks' solution for 1 day, 4 days, and 16 days. Each test group of the three different periods of immersion time has five specimens, the compressive strength of which was measured by using a AGS-500D mechanical tester (Shimadzu Co., Ltd., Kyoto, Japan) immediately following the removal thereof from the Hanks' solution without drying. The CPC paste in the mold was compressed with a maximum pressure of 166.6 MPa, and in the course of the compression the compression speeds were about 5 mm/min during 0~104.1 MPa; 3 mm/min during 104.1~138.8 MPa; 1 mm/min during 138.8~159.6 MPa: and 0.5 mm/min during 159.6~166.6 MPa. The measured wet specimen compressive strength is listed Table 1.

TABLE 1

| Immersion time (Day) | Compressive strength (MPa) | Standard deviation (MPa) |
|---|---|---|
| No immersion | 37.3* | 0.6 |
| 1 day | 149.2 | 12.9 |
| 4 days | 122.7 | 6.7 |
| 16 days | 116.4 | 7.7 |

*This value was measured before the compressed CPC blocks were immersed in the Hanks' solution, and it was substantially the same for the compressed CPC blocks not immersed in the Hanks' solution measured a few days after the preparation.

It can seen from Table 1 that the compressive strength of the compressed CPC blocks is increased remarkably after one-day immersion in comparison with the non-immersed block, and declines a little for a longer immersion time.

EXAMPLE 2

Effect of Immersion Solution on Compressive Strength of CPC Block

The procedures of EXAMPLE 1 were repeated except that the immersion solution was varied, and the maximum pressure used to compress the CPC paste in the mold was changed from 166.6 to 156.2 MPa. The immersion solutions used in this example were Hanks' solution (37° C., pH=7), $(NH_4)_2HPO_4$ solution (37° C., pH=8), and HCl solution (37° C., pH=4). The period of immersion was one day. The results are listed in Table 2.

TABLE 2

| Immersion solution | Compressive strength (MPa) | Standard deviation (MPa) |
|---|---|---|
| Hanks' solution | 138.0 | 8.2 |
| $(NH_4)_2HPO_4$ | 122.9 | 3.1 |
| HCl | 141.7 | 7.0 |

The results in Table 2 show that all the three immersion solutions have same level of effectiveness.

EXAMPLE 3

Effect of Whiskers on Compressive Strength of TTCP/DCPA-Based CPC Block

The procedures of EXAMPLE 1 were repeated by using the C—CPC powder prepared in PREPARATIVE EXAMPLE 2 and the ND-CPC powder prepared in PREPARATIVE EXAMPLE 3. The maximum pressure used to compress the CPC paste in the mold in this example was 156.2 MPa. The results for one-day immersion time are listed in Table 3.

TABLE 3

| CPC powder | Compressive strength (MPa) | Standard deviation (MPa) |
|---|---|---|
| C-CPC (no whisker) | 62.3 | 5.0 |
| ND-CPC (with whisker) | 138.0 | 8.2 |

It can be seen from Table 3 that the compressive strength, 62.3 MPa, of the immersed compressed CPC block prepared from the conventional CPC powder (no whisker) is about 1.7 times of that (37.3 MPa) of the non-immersed compressed CPC block in Table 1, and the compressive strength, 138.0 MPa, of the immersed compressed CPC block prepared from the non-dispersive CPC powder (with whisker) is about 3.7 times of that of the non-immersed compressed CPC block in Table 1.

EXAMPLE 4

Effect of Whiskers on Compressive Strength of TTCP-Based CPC Block $Ca_4(PO_4)_2O$ (TTCP) powder as synthesized in PREPARATIVE EXAMPLE 1 was sieved with a #325 mesh. The sieved powder has an average particle size of about 10 µm. To the TTCP powder HCl aqueous solution (pH=0.8) was added according to the ratio of 1 g TTCP/13 ml solution. The TTCP powder was immersed in the HCl aqueous solution for 12 hours, filtered rapidly and washed with deionized water, and filtered rapidly with a vacuum pump again. The resulting powder cake was dried in an oven at 50° C. The dried powder was divided into halves, ground for 20 minutes and 120 minutes separately, and combined to obtain the non-dispersive TTCP-based CPC powder, the particles of which have whisker on the surfaces thereof. A setting solution of diammonium hydrogen phosphate was prepared by dissolving 20 g of diammonium hydrogen phosphate, $(NH_4)_2HPO_4$, in 40 ml deionized water. The procedures in EXAMPLE 1 were used to obtain the wet specimen compressive strength for one-day immersion time, wherein the maximum pressure to compress the CPC paste in the mold was 156.2 MPa. The results are-shown in Table 4.

TABLE 4

| CPC powder | Compressive strength (MPa) | Standard deviation (MPa) |
|---|---|---|
| TTCP (no whisker) | 79.6 | 8.8 |
| TTCP (with whisker) | 100 | 4.2 |

The trend same as in the TTCP/DCPA-based CPC powder in EXAMPLE 3 can be observed in Table 4.

EXAMPLE 5

Effect of Molding Pressure on Compressive Strength of ND-CPC Block (in Low Pressure Regime: 0.09~3.5 MPa)

The procedures of EXAMPLE 1 were repeated except that the maximum pressure used to compress the CPC paste in the mold was changed from 166.6 MPa to the values listed in Table 5. The period of immersion was one day. The results are listed in Table 5.

TABLE 5

| Pressure for compressing the CPC paste in mold (MPa) | Compressive strength (MPa) | Standard deviation (MPa) |
|---|---|---|
| 0.09 | 12.3 | 2.0 |
| 0.35 | 16.0 | 2.3 |
| 0.7 | 20.7 | 2.5 |
| 1.4 | 26.4 | 1.4 |
| 3.5 | 35.2 | 3.7 |

The data in Table 5 indicate that the compressive strength of the CPC block increases as the pressure used to compress the CPC paste in the mold increases.

EXAMPLE 6

Effect of Reducing Liquid/Powder Ratio During Compression of the CPC Paste in the Mold on Compressive Strength of ND-CPC Block The procedures of EXAMPLE 1 were repeated except that the maximum pressure used to compress the CPC paste in the mold was changed from 166.6 MPa to the values listed in Table 6. The liquid leaked from the mold during compression was measured, and the liquid/powder ratio was re-calculated as shown in Table 6. The period of immersion was one day. The results are listed in Table 6.

TABLE 6

| Pressure for compressing the CPC paste in mold (MPa) | L/P ratio (after a portion of liquid removed) | Compressive strength (MPa) | Standard deviation (MPa) |
|---|---|---|---|
| 1.4 | 0.25 | 26.4 | 1.4 |
| 34.7 | 0.185 | 75.3 | 3.9 |
| 69.4 | 0.172 | 100.4 | 6.8 |
| 156.2 | 0.161 | 138.0 | 8.2 |
| 166.6 | 0.141 | 149.2 | 12.9 |

The data in Table 6 show that the compressive strength of the CPC block increases as the liquid/powder ratio decreases during molding.

EXAMPLE 7

Effect of Temperature of the Immersion Solution on Compressive Strength of CPC Block The procedures of EXAMPLE 1 were repeated except that the temperature of the immersion solution was varied, and the maximum pressure used to compress the CPC paste in the mold was changed from 166.6 to 156.2 MPa. Two different temperatures of the Hanks' solution were used, one is 37° C., and the other is 90° C. The period of immersion was one day. The results are listed in Table 7.

TABLE 7

|  | Compressive strength (MPa) | Standard deviation (MPa) |
| --- | --- | --- |
| Hanks' solution-37° C. | 138.0 | 8.2 |
| Hanks' solution-90° C. | 113.7 | 4.1 |

The results in Table indicate that a higher temperature adversely affect the compressive strength of the CPC block.

EXAMPLE 8

Effect of Post-Heat Treatment on Compressive Strength of CPC Block

The procedures of EXAMPLE 1 were repeated. The period of immersion was one day. The CPC blocks after removing from the Hanks' solution were subjected to post-heat treatments: 1) 50° C. for one day; and 2) 400° C. for two hours with a heating rate of 10° C. per minute. The results are listed in Table 8.

TABLE 8

|  | Compressive strength (MPa) | Standard deviation (MPa) |
| --- | --- | --- |
| No post-heat treatment | 149.2 | 12.9 |
| 50° C., one day | 219.4 | 16.0 |
| 400° C., two hours | 256.7 | 16.2 |

It can be seen from Table 8 that the post-heat treatment enhances the compressive strength of the CPC block.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method for making a molded calcium phosphate article comprising impregnating a rigid shaped article of calcium phosphate with an impregnating liquid for a period of time so that a compressive strength of the resulting impregnated article removed from the impregnating liquid is increased compared to that of said rigid shaped article without said impregnating treatment, wherein the rigid shaped article of calcium phosphate is a molded article from a paste of calcium phosphate cement.

2. The method according to claim 1, wherein the impregnating liquid is an acidic solution, a basic solution, a physiological solution, an organic solvent, or a substantially pure water.

3. The method according to claim 2, wherein the impregnating liquid comprises at least one of Ca and P sources.

4. The method according to claim 2, wherein the impregnating liquid is a Hanks' solution, a HCl aqueous solution or an aqueous solution of $(NH_4)_2HPO_4$.

5. The method according to claim 1, wherein the impregnating is carried out for a period longer than 10 minutes.

6. The method according to claim 5, wherein the impregnating is carried out for about 12 hours to 96 hours.

7. The method according to claim 1, wherein the impregnating is carried out at room temperature or at a temperature between about 30 and 90° C.

8. The method according to claim 4, wherein said calcium phosphate cement comprises one or more calcium phosphates selected from the group consisting of alpha-tricalcium phosphate (α-TCP), beta-tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.

9. The method according to claim 8, wherein the calcium phosphate cement comprises at least one calcium phosphate particle having calcium phosphate whiskers on the surface of said calcium phosphate particle, wherein said calcium phosphate whiskers have a length of about 1–5000 nm and a width of about 1–500 nm.

10. The method according to claim 4, wherein said paste is formed by mixing said calcium phosphate cement with a setting liquid.

11. A method for making a molded calcium phosphate article comprising the following steps:
(a) preparing a powder comprising at least one Ca source and at least one P source, or at least one calcium phosphate source;
(b) mixing said powder with a setting liquid to form a paste, wherein said paste undergoes a hardening reaction;
(c) molding said paste into an article in a mold of a desired shape and size before said hardening reaction is complete;
(d) impregnating the resulting hardened article from step (c) with an impregnating liquid to allow strength of said article to increase; and
(e) removing said article from said impregnating liquid.

12. The method according to claim 11, wherein said calcium phosphate source in step (a) comprises one or more calcium phosphates selected from the group consisting of alpha-tricalcium phosphate (α-TCP), beta-tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.

13. The method according to claim 11, wherein the calcium phosphate source comprises at least one calcium phosphate particle having calcium phosphate whiskers on the surface of said calcium phosphate particle, wherein said calcium phosphate whiskers have a length of about 1–5000 nm and a width of about 1–500 nm.

14. The method according to claim 11, wherein the setting liquid in step (b) is an acidic solution, a basic solution, or a substantially pure water.

15. The method according to claim 14, wherein said acidic solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate ($NaH_2PO_4.H_2O$), sodium dihydrogen phosphate dihydrate, sodium dihydrogen phosphate dehydrate, potassium dihydrogen phosphate ($KH_2PO_4$), ammonium dihydrogen.phosphate ($NH_4H_2PO_4$), malic acid, acetic acid, lactic acid, citric acid, malonic acid, succinic acid, glutaric acid, tartaric acid, oxalic acid and their mixture.

16. The method according to claim 14, wherein said basic solution is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4.12H_2O$), dipotassium hydrogen phosphate ($K_2HPO_4$), potassium hydrogen phosphate trihydrate ($K_2HPO_4.3H_2O$), potassium phosphate tribasic ($K_3PO_4$), diammonium hydrogen phosphate (($NH_4)_2HPO_4$), ammonium phosphate trihydrate (($NH_4)_3PO_4.3H_2O$), sodium bicarbonate ($NaHCO_3$), sodium hydrogen carbonate ($NaHCO_3$), sodium carbonate $Na_2CO_3$, and their mixture.

17. The method according to claim 11, wherein step (c) further comprises removing said article from said mold.

18. The method according to claim 11, wherein step (c) further comprises removing a portion of liquid from said paste, so that a liquid/powder ratio of said paste decreases.

19. The method according to claim 11, wherein step (c) further comprises pressurizing said paste in said mold before said hardening reaction is complete to remove a portion of liquid from said paste, so that a liquid/powder ratio of said paste decreases.

20. The method according to claim 19, wherein step (c) further comprises heating said paste during said pressurizing.

21. The method according to claim 11, wherein step (c) further comprises heating said paste during molding.

22. The method according to claim 11, wherein step (d) further comprises heating the impregnating liquid during said impregnating.

23. The method according to claim 22, wherein step (d) further comprises heating the impregnating liquid at a temperature between about 30 and 90° C. during said impregnating.

24. The method according to claim 11 further comprising drying said article after removing said article from said impregnating liquid.

25. The method according to claim 11 further comprising heating said article after removing said article from said impregnating liquid.

26. The method according to claim 25, wherein said article after being removed from said impregnating liquid is heated at a temperature between 50 and 500° C.

27. The method according to claim 11, wherein the impregnating liquid in step (d) is an acidic solution, a basic solution, a physiological solution, an organic solvent, or a substantially pure water.

28. The method according to claim 27, wherein the impregnating liquid comprises at least one of Ca and P sources.

29. The method according to claim 27, wherein the impregnating liquid is a Hanks' solution, a HCl aqueous solution or an aqueous solution of ($NH_4)_2HPO_4$.

30. The method according to claim 11, wherein the impregnating in step (d) is carried out for a period longer than 10 minutes.

31. The method according to claim 30, wherein the impregnating is carried out for about 12 hours to 96 hours.

32. The method according to claim 11, wherein the impregnating in step (d) is carried out at room temperature.

* * * * *